United States Patent [19]

Pusztai-Carey et al.

[11] Patent Number: 5,356,788
[45] Date of Patent: Oct. 18, 1994

[54] ISOLATION, QUANTITATION AND PURIFICATION OF INSECTICIDAL PROTEINS FROM BACILLUS THURINGIENSIS

[75] Inventors: Marianne Pusztai-Carey; Paul R. Carey, both of Ottawa; Timothy Lessard, Richmond; Makoto Yaguchi, Ottawa, all of Canada

[73] Assignee: Her Majesty the Queen in right of Canada, as represented by the National Research Council of Canada, Ottawa, Canada

[21] Appl. No.: 102,491

[22] Filed: Aug. 5, 1993

Related U.S. Application Data

[63] Continuation of Ser. No. 836,967, Feb. 19, 1992, abandoned, which is a continuation-in-part of Ser. No. 493,453, Mar. 14, 1990, abandoned.

[51] Int. Cl.$^5$ .......... C12Q 1/37; C12N 1/20; G01N 33/567
[52] U.S. Cl. .......... 435/23; 435/803; 435/252.33; 435/317.1; 435/69.1; 436/504; 436/548
[58] Field of Search .......... 435/23, 803, 252.3, 435/252.33, 317, 69.1; 424/93; 436/504, 548

[56] References Cited

U.S. PATENT DOCUMENTS

| | | | |
|---|---|---|---|
| 4,467,036 | 8/1984 | Schnepf et al. | 435/252.33 |
| 4,717,653 | 1/1988 | Webster, Jr. | 435/803 |
| 4,853,331 | 8/1989 | Herrnstadt et al. | 435/252.3 |
| 4,865,981 | 9/1989 | Herrnstadt et al. | 435/252.3 |
| 4,910,136 | 3/1990 | Herrnstadt et al. | 435/252.3 |
| 5,010,001 | 4/1991 | Pollock | 435/252.33 |

FOREIGN PATENT DOCUMENTS

WO 90/13651  11/1990  PCT Int'l Appl.

OTHER PUBLICATIONS

Bernhard, K. "Quantitative Determination of . . . " World Journal of Microbiology & Biotechnology, 8, 24–29.

Hickle, L. A. et al "Analytical chemistry of *Bacillus thuringiensis*,"ACS Symposium series 432, Wash. D.C. 1990, pp. 1–8.

*Primary Examiner*—Michael G. Wityshyn
*Assistant Examiner*—Louise N. Leary
*Attorney, Agent, or Firm*—Nixon & Vanderhye

[57] ABSTRACT

A process for identifying proteinaceous protoxins expressed by *Bacillus thuringiensis* genes is disclosed. According to the process, daughter toxins are first generated by subjecting a protoxin-containing material, such as parasporal crystals of *Bacillus thuringiensis,* to limited proteolysis with a proteolytic enzyme in an aqueous suspension having a pH above 9.5. The daughter toxins are then separated by high performance anion-exchange liquid chromatography at a constant pH in excess of 10 in an increasing gradient of a salt, preferably sodium chloride. The gradient conditions, which are specific for the column used, are achieved by employing a series of buffers having increasing concentration of the salt and introduced at a predetermined time and rate. The procedure provides a chromatogram showing clearly identifiable peaks of toxins and permits therefore the qualitative and quantitative characterization of the original mixture and isolation of the individual toxins. By this it provides means of screening and testing new *Bacillus thuringiensis* isolates, both single - and multigene, and monitoring the level of expression of known genes from a known strain. The digestion and isolation conditions permit the production of the toxins in a biologically fully active state.

25 Claims, 11 Drawing Sheets

Bacillus thuringiensis toxins

```
          29 31       41         51         61         71         81         91        100
4.5 gene   IE TGYTPIDISL SLTQFLLSEF VPGAGFVLGL VDIIWGIFGP SQWDAFPVQI EQLINQRIEE FARNQAISRL
          29
5.3 gene   IE TGYTPIDISL SLTQFLLSEF VPGAGFVLGL VDIIWGIFGP SQWDAFLVQI EQLINQRIEE FARNQAISRL
          29
6.6 gene   IE TGYTPIDISL SLTQFLLSEF VPGAGFVLGL VDIIWGIFGP SQWDAFLVQI EQLINQRIEE FARNQAISRL 101        111        121        131        141        151        161       170
4.5 gene   EGLSNLYQIY AESFREWEAD PTNPALREEM RIQFNDMNSA LTTAIPLLAV QNYQVPLLSV YVQAANLHLS
5.3 gene   EGLSNLYQIY AESFREWEAD PTNPALREEM RIQFNDMNSA LTTAIPLFAV QNYQVPLLSV YVQAANLHLS
6.6 gene   EGLSNLYQIY AESFREWEAD PTNPALREEM RIQFNDMNSA LTTAIPLFAV QNYQVPLLSV YVQAANLHLS 171        181        191        201        211        221        231       240
4.5 gene   VLRDVSVFGQ RWGFDAATIN SRYNDLTRLI GNYTDYAVRW YNTGLERVWG PDSRDWIRYN QFRRELTLTV
5.3 gene   VLRDVSVFGQ RWGFDAATIN SRYNDLTRLI GNYTDHAVRW YNTGLERVWG PDSRDWVRYN QFRRELTLTV
6.6 gene   VLRDVSVFGQ RWGFDAATIN SRYNDLTRLI GNYTDYAVRW YNTGLERVWG PDSRDWVRYN QFRRELTLTV 241        251        261        271        281        291        301       310
4.5 gene   LDIVSLFSNY DSRRYPIRTV SQLTREIYTN PVLENFDGSF RGMAQRIEQN IRQPHLMDIL NSITIYTDVH
5.3 gene   LDIVALFPNY DSRTYPIRTV SQLTREIYTN PVLENFDGSF RGSAQGIEGS IRSPHLMDIL NSITIYTDAH
6.6 gene   LDIVALFPNY DSRRYPIRTV SQLTREIYTN PVLENFDGSF RGSAQGIERS IRSPHLMDIL NSITIYTDAH 311        321        331        341        351        360        370       380
4.5 gene   RGENYWSGHQ ITASPVGFSG PEFAFPLFGN AGNAAPPVLV SLT-GLGIFR TLSSPLYRRI ILGSGPNNQEL
                                                                361        371       380
5.3 gene   RGFYYWSGHQ IMASPVGFSG PEFTFPLYGT MGNAAPQQRI VAQLGQGVYR TLSSTLYRRP FNI-GINNQQL
                                                                361        371       380
6.6 gene   RGYYYWSGHQ IMASPVGFSG PEFTFPLYGT MGNAAPQQRI VAQLGQGVYR TLSSTLYRRP FNI-GINNQQL
```

FIG. 10A

```
              381         392        402        412        422        432        441       449
4.5 gene      FVLDGTEFSFASLTTNLPSTI YRQRGTVDSL DVIPPQDNSV PPRAGFSHRL SHVTML-SQA AGA-VYTLRA
              381                  391        401        411        421        431        441       450
5.3 gene      SVLDGTEFAY GTSSNLPSAV YRKSGTVDSL DEIPPQNNNV PPRQGFSHRL SHVSMFRSGF SNSSVSIIRA
              381        391        401        411        421        431        441       450
6.6 gene      SVLDGTEFAY GTSSNLPSAV YRKSGTVDSL DEIPPQNNNV PPRQGFSHRL SHVSMFRSGF SNSSVSIIRA 450        460        470        480        490        500        510       519
4.5 gene      PTFSWQHRSA EFNNIIPSSQ ITQIPLTKST NLGSGTSVVK GPGFTGGDIL RRTSPGQIST LRVNITAPLS
              451        461        471        481        491        501        511       520
5.3 gene      PMFSWIHRSA EFNNIIPSSQ ITQIPLTKST NLGSGTSVVK GPGFTGGDIL RRTSPGQIST LRVNITAPLS
              451        461        471        481        490        500        510       520
6.6 gene      PMFSWIHRSA EFNNIIASDS ITQIPAVKGN FLFNG-SVIS GPGFTGGDLV RLNSSGNNIQ NRGYIEVPIHF 520        530        540        550        560        570       579
4.5 gene      QRYRVRIRYA STTNLQFHTS IDGRPINQGN FSATM      SSGSN LQSGSFRTVG FTTPFNFSNG
              521        531        541        551        561        571       580
5.3 gene      QRYRVRIRYA STTNLQFHTS IHGRPINQGN FSATM      SSGSN LQSGSFRTVG FTTPFNFSNG
                         535        540                  565
6.6 gene      PSTSTRYRVRVRYA     SVTPI HLNVNWGNSSI FSNTVPATATSLDN LQSSDF     GYFESANAFT  580

580        590        600        610        620
4.5 gene      SSVFTLSAHV FNSGNEVYID RIEFVPAEVT FEAEYDLERA QK 621
              581        591        601        611        621
5.3 gene      SSVFTLSAHV FNLGNEVYID RIEFVPAKVT FEAEYDLERA QK 622
              581        592        602        612        622
6.6 gene      SSLGNIVGVRN FSGTAGVIID RFEFIPVTAT LEAEYNLERA QK 623
```

FIG. IOB

ISOLATION, QUANTITATION AND PURIFICATION OF INSECTICIDAL PROTEINS FROM *BACILLUS THURINGIENSIS*

This is a continuation of patent application Ser. No. 07/836,967, filed Feb. 19, 1992, now abandoned, which is a continuation-in-part of patent application Ser. No. 07/493,453, filed Mar. 14, 1990, now abandoned.

BACKGROUND OF THE INVENTION

The invention relates to the identification, quantitation and purification of insecticidal proteins from *Bacillus thuringiensis*, in particular from multigene strains of *Bacillus thuringiensis*.

*Bacillus thuringiensis* (hereinafter abbreviated Bt) is a gram-positive soil bacterium characterized by its ability to produce large crystalline parasporal inclusions during sporulation. These inclusions consist of proteins exhibiting a highly specific insecticidal activity (protoxins).

Many Bt strains with different insect host toxicity spectra have been identified. Numerous strains are active against larvae of certain members of the Lepidoptera (Bt strains active against over 100 species of lepidopterans have been identified to date), but strains showing toxicity against dipteran or coleopteran species are also known.

Bt parasporal inclusions have proven to be a valuable alternative to conventional insecticides. They are highly toxic to the target insects and harmless to the environment owing to their specificity. Other insect orders, animals and plants appear to be unaffected by the toxic crystal proteins. Various formulations of Bt have been used for more than two decades as biological insecticides to control pests in agriculture and forestry and, more recently, to control insect vectors of a variety of human and animal diseases.

Bt produces several types of toxins, the precise biochemical nature of which may vary from strain to strain. Some of them, in particular $\alpha$- and $\beta$-exotoxins, are toxic to a variety of insect orders or to many cell types. The parasporal crystal inclusion toxins (also called $\delta$-endotoxins), which are proteins, have a more limited and specific host range. When consumed by a larva, Bt crystalline inclusions dissolve in the larval midgut and rapidly undergo proteolytical conversion into smaller toxic polypeptides (in the 23–80 kD molecular weight range) in the insect midgut. The produced toxin species interact with midgut epithelium cells of the host insect, generating pores in the cell membrane and disturbing the osmotic balance. The epithelium cells swell and lyse. The larva stops feeding and eventually dies. For several Bt toxins specific high-affinity binding sites have been demonstrated to exist on the midgut epithelium of susceptible insects, which could explain the extreme specificity of these toxins.

It has become clear in recent years that Bt is provided with a surprisingly large and variable family of insecticidal proteins. Data obtained using several experimental methods indicate that crystal protein genes in many subspecies of Bt that are toxic to lepidopterans are located on one or more large plasmids; in some subspecies, the gene may be located on the chromosome. The fact that the genes for the Bt protoxins are usually plasmid borne has made Bt a favourite candidate for genetic manipulations. This has resulted recently, among other things, in generating insect-resistant transgenic crop plants capable of expressing Bt crystal protein genes.

It has also become clear in recent years that many Bt strains contain several closely related genes coding for protoxins. For example Bt var. kurstaki NRD-12 strain is a three-gene strain. The presence of several such genes results in the production by a single Bt strain of several protoxins closely related by their amino acid sequences. Enzymatic action of proteolytic enzymes on such a mixture of protoxins, either in vitro or in the insect midgut, produces several toxins which may only differ by a few amino acid residues, which makes the obtained mixture of toxins difficult to separate. However, since these small differences frequently occur in key regions of the toxin sequence, they may result in significantly different toxicities towards a selected insect target. As the composition of the mixture of toxins produced by a multigene strain of Bt or the expression level of the individual toxins may vary with fermentation conditions, so may its relative toxicity to various insects, and, as a consequence, the host range of the multigene Bt strain. It becomes therefore important to monitor and quantitate different toxins present in endotoxin crystals, in order to optimize the production of the most wanted toxin from a multigene producer.

Various attempts to purify entomocidal toxins from $\delta$-endotoxins of various strains of Bt are known from the prior art. The proposed methods typically include a digestion of crystalline inclusions of Bt with a proteolytic enzyme, such as trypsin, or insect digestive juices, followed by separation of the products of hydrolysis by various analytical procedures, such as electrophoresis, gel filtration and ion exchange chromatography. However, none of these methods demonstrated the ability to separate and purify closely related toxins obtained from a multigene strain of Bt.

Similarly, numerous methods of qualitative and quantitative characterization of Bt strains have been proposed. They involve, for example, the use of flagellar antibodies, probing for the genes with DNA probes or measuring the level of RNA production. These methods, although useful for characterization and classification purposes, are not satisfactory for quantitation of gene expression and monitoring the viability of a given strain or producing individual toxin standards for analyzing insecticidal activity, synergism, membrane studies or insect resistance.

More specifically in Fullmer, C. S. and Wasserman, R. H. Analytical Peptide Mapping by High Performance Liquid Chromatography. Application to intestinal calcium-binding proteins. J. Biol. Chem. 254, 7208–7212 (1979) a peptide mapping technique is described involving an exhaustive enzymatic digestion to provide a mixture of peptides. The analysis of the peptide mixture is carried out by reverse-phase HPLC, in association with an acid and an organic solvent.

In another reference, Yamamoto, T. Identification of Entomocidal Toxins of *Bacillus thuringiensis* by High Performance Liquid Chromatography. J. Gen. Microbiol. 129, 2595–2603 (1983), peptide mapping using the same Fullmer et al methodology is described. For example, see page 2601, line 5 under FIG. 4 where it is stated "A peak representing the proteinase resistant core could not be located". It is emphasized here that the use of organic solvent, either permanently reduces, or completely destroys, the biological activity of the toxins.

In a further reference, Yamamoto, T., Ehmann, A., Gonzalez, J. M. Jr. and Carlton, B. C. Expression of Three Genes Coding for 135-Kilodalton Entomocidal Proteins in *Bacillus thuringiensis kurstaki*. Current Microbiol. 17, 5-12 (1988), the same peptide mapping methodology is also followed. In this reference, the protoxin(s) is/are pre-purified, prior to trypsin hydrolysis. Following hydrolysis, the toxin mixture is denatured in urea and re-digested by trypsin for peptide mapping using reverse-phase HPLC (the peptides were solubilized in acid and eluted in acid/acetonitrile mixtures). As mentioned, above, this destroys the biological activity of the toxin. Unfortunately, the resultant peptide mapping, using single gene standards to interpret the results from multi-gene strains, failed to recognize the presence of the cryIA(c)[6.6] gene product in the strain kurstaki HD-1. This gene and its protein toxin is an important component, shown to be present by other researchers.

Further, in Hernstadt, C. and Wilcox E. Cloning and Expression of *Bacillus thuringiensis* Toxin gene Toxic to Beetles of the Order Coleoptera. U.S. Pat. No. 4,853,331 (1989) the cloning of a single gene and producing a single Bt protein by *E. Coli* host cells is described. The toxin is purified by affinity chromatography.

To the contrary, none of the aforementioned techniques will provide for the identification, quantitation and purification of protoxins, expressed by a Bt gene, while retaining the biological activity of the toxin. In fact, these references have a different purpose in mind, namely peptide mapping, wherein destruction of the biological activity of the toxin is irrelevant. However, in our invention, the biological activity of the toxin must remain substantially intact. Accordingly we cannot use the reverse-phase HPLC technique employed in these prior art techniques.

SUMMARY OF THE INVENTION

The present invention provides a process for identifying a protoxin expressed by a *Bacillus thuringiensis* gene, which process comprises hydrolyzing a *Bacillus thuringiensis* protoxin-containing material with a proteolytic enzyme in an aqueous suspension at a pH in the range of 10 to 12 to generate a solubilized daughter toxin, subjecting the daughter toxin to high performance anion-exchange liquid chromatography at a substantially constant pH in the range of 10 to 12, and under aqueous conditions corresponding to the use of a first eluent containing only a buffer and the gradual introduction over a predetermined period of time of at least one other eluent containing the buffer and a suitable salt, the changes in time of the concentration of the salt in the eluent being such that the daughter toxin, in biologically active state, is separated from other products of hydrolysis, and identifying, and where required quantifying, the protoxin from the chromatographic signals produced by the daughter toxin.

It will be appreciated that the term "daughter toxin" may cover a mixture of protoxins or an individual protoxin, depending on the starting material. Thus, when a multigene strain of Bt is involved, a mixture of protoxins is involved, and when a single gene strain of Bt is used, a single protoxin is involved.

Thus, a method has now been found according to which closely related toxins from a multigene strain of Bt can be separated, identified and purified in their biologically active state. According to the method purified protein crystals or a crude fermentation mixture from, for instance, a multigene strain of Bt is subjected directly to the action of proteolytic enzyme at pH of from about 10 to about 12, preferably 10.5 This proteolytic digestion liberates the toxins, which are then subjected to anion exchange high performance liquid chromatography (HPLC) at a pH range of 10 to 12, preferably in a range of 10.5 to 11.5, using an anion exchange column. The elution of the toxins is carried out with a buffer solution of suitable pH in an increasing gradient of a salt, preferably sodium chloride. The procedure provides a chromatogram showing clearly identifiable peaks characteristic of toxins and therefore permits the qualitative and quantitative characterization of the original mixture. The separation process can be scaled up using semipreparative or preparative columns, thus permitting the isolation of pure active toxins in large quantities.

Although the most used applications of the invention may be in the separation or identification of individual toxins from a mixture of toxins obtained from a multigene strain of Bt, the invention can be used to characterize a single toxin obtained from a single-gene strain of Bt. When the toxin or toxins from the single-gene or multi-gene strain of Bt, respectively, are characterized, the strain of Bt is also characterized.

According to the present method also the level of expression of known toxins from a known Bt strain can be determined and the viability of the strain can be monitored.

BRIEF DESCRIPTION OF THE DRAWINGS

FIGS. 10A and 10B show amino acid sequence of 3 toxins of Bt kurstaki NRD-12 strain and the peptide fragments identified from the isolated single protein toxins.

DESCRIPTION OF THE PREFERRED EMBODIMENTS

Figure 1:
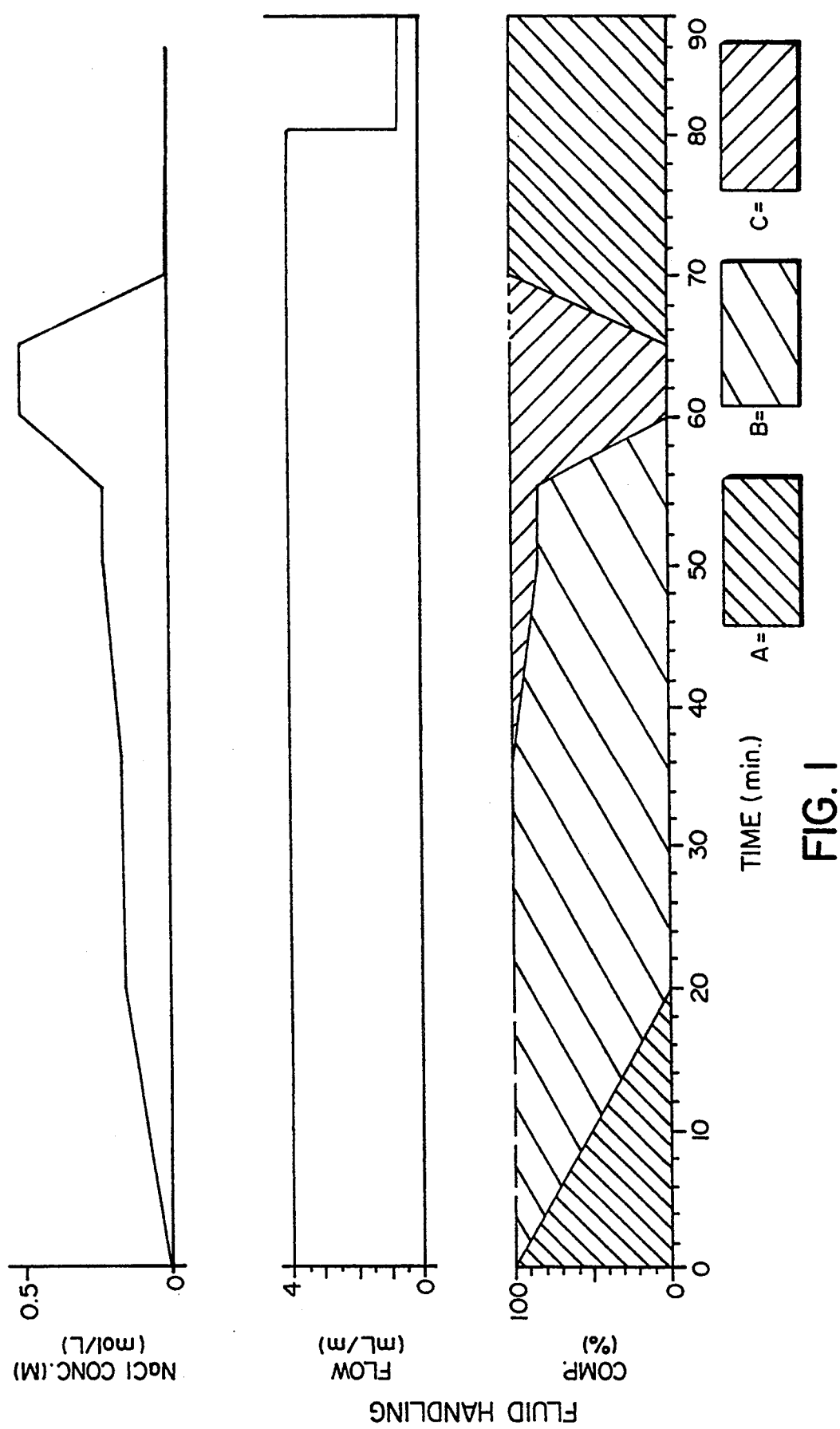
FIG. 1 represents gradient conditions of chromatographic separation according to one preferred embodiment of the invention, using Protein PAK DEAE 5 PW semipreparative column.

One embodiment according to the invention comprises typically the following steps:

a) purification of Bt endotoxin crystals from a fermentation mixture;
b) direct proteolytic enzyme digestion of the crystals; and
c) anion exchange HPLC separation of the products of hydrolysis.

Although the material digested by proteolytic enzymes is normally crystalline endotoxin purified from crude fermentation mixtures, such a purification, although preferred, is not essential. Recognizable peaks characteristic of toxins in the anion exchange HPLC elution pattern can be also obtained using a crude Bt material separated from the fermentation broth prior to enzymatic digestion.

The purified crystals or washed crude material are then subjected directly to hydrolysis with a proteolytic enzyme, such as trypsin, chymotrypsin or elastase. Trypsin is the preferred enzyme. Also insect gut juices, such as gut juice from silk worm (Bombyx mori) are effective. Each particular enzyme gives a slightly different set of toxins, since each has a unique specificity with respect to endotoxin proteins. Commercially available preparations of enzymes may be used. The concentration range of the enzyme is from 0.1 to 2 mg/mL, preferably 1 mg/mL.

The temperature of digestion of the endotoxin with the proteolytic enzyme is not critical and may vary from 20° to 40° C., preferably, about 37° C. The duration of hydrolysis is also not critical but should be long enough to assure a nearly complete liberation of toxins under given pH, temperature and enzyme concentration conditions. For trypsin digestion, the time of digestion is about 10 minutes to 12 hours.

The hydrolysis can be carried out in an unbuffered or buffered solution having pH in the specified range. Examples of suitable solutions are 3-cyclohexylamino-1-propanesulfonic acid/NaOH buffer (CAPS) borate buffer or unbuffered solution of NaOH. Not all solutions are equally efficient. Since the toxins released during hydrolysis are apparently hydrophobic and poorly soluble in water, it is preferable that the solution contains components which assist solubilization of the toxin protein molecules. One example of such a component is 3-cyclohexylamino-1-propanesulfonic acid (CAPS). The preferred solution is 0.1M CAPS/NaOH buffer having pH 10.5.

After hydrolysis the solid components of the reaction mixture are removed, for example by centrifugation and filtration. Samples of the filtrate (supernatant) are used for HPLC analysis. The pellet should not contain any recognisable inclusion body by phase contrast microscope (as a sign of complete digestion).

The HPLC separation of the products of proteolytic hydrolysis provides a fingerprint by which the toxins can be identified and quantified. To achieve an adequate solubility of the toxins the separation must be conducted at pH not lower than about 10, preferably 10.5 to 11.5. On the other hand, pH should not be higher than about 12, to avoid the denaturation of the toxins and to assure the proper operation of the column. In the specified range of pH the molecules of toxins are negatively charged and the separation is carried out as a liquid-solid anion exchange chromatography. The use of HPLC technique allows the achieving of the separation in short periods of time.

It should be noted that although the separation of the toxins according to the invention can be carried out at any value of pH in the indicated broad range, increasing the pH above the preferred range of 10.5 to 11.5 unnecessarily increases the danger of denaturation of the separated proteins and irreversible damages to the column. On the other hand, decreasing the pH below 10.5 increases the danger of toxins being precipitated in the HPLC column, at least partially, which adversely affects the reliability of quantitative determinations. For these reasons the pH range of about 10.5 to 11.5 is considered to be the optimum.

Columns packed with anion exchangers are used for the separation. Both weak and strong anion exchangers can be used. Weak anion exchangers are preferred. Diethylaminoethyl poly(methyl methacrylate) is especially preferred.

The elution of the toxins from the column is carried out at room temperature employing a suitable buffer, in an increasing gradient of a salt, such as sodium chloride. The employed buffer is in first place responsible for maintaining the required pH of the eluent.

However, it appears that not only the pH but also the composition of the buffer is important for successful separation. In one preferred embodiment, 0.05M CAPS/NaOH buffer (pH=10.5) is employed. However, it will be appreciated that alternative buffer systems with a new set of elution conditions may be found.

The conditions of salt gradient are specific for the column used. These conditions are normally achieved by employing a series of buffers having increasing concentration of the salt and introduced in a predetermined order and at a predetermined time.

The salt used in the separation should bind rather strongly to the column, but should not bind to or otherwise adversely affect the separated proteins. Examples of suitable salts include sodium chloride, potassium chloride, ammonium chloride and sodium acetate. Bromides and iodides may also be used. Sodium chloride is preferred. Some salts, for instance calcium salts, bind to some proteins and affect the properties of the protein. These salts are therefore not suitable. Selection of a suitable salt will present no problem to a person skilled in the art.

According to the most preferred embodiment of the invention, the elution from the chromatographic column is effected, immediately after hydrolysis, in two stages. A first eluent is 0.05M CAPS/NaOH buffer, pH 11.5, followed by a second eluent of 0.05M CAPS/NaOH buffer and 0.5M NaOl, pH 11.5. The two eluents are simultaneously introduced into the column in such a manner that the amount of the second eluent increases linearly from 0 to 33% over a period of 25 to 40 minutes, depending upon the nature of the sample. This step was followed by a 20–50 minute isocratic period while the toxinx are eluting.

Parts of the eluate corresponding to candidate peaks may be collected, concentrated and reinjected to establish identity and purity of the separated toxins. When the separation is carried out using a semipreparative or preparative column, an active, native toxin may be isolated and collected.

The method of rapid identification, quantitation and purification of toxins resulting from proteolytic hydrolysis of protoxins of endotoxin crystals is of considerable interest for the art. It provides means of screening and testing new Bt isolates by a rapid comparison against known strains. It also allows experiments in the manipulation of fermentation conditions to optimise the production of the most wanted toxin from multigene strains. It also enables producers to characterize the Bt toxins produced by competitors' strains. Since separated toxins may be collected in pure and active form, the method will permit testing of individual purified toxins and mixtures of individual toxins prepared in a specified and controlled manner. Although of particular interest for multigene strains of Bt, the method has obviously similar application for single gene strains of Bt and for analysis of inclusion bodies from cloned Bt genes, e.g. in *E. coli.*

EXPERIMENTAL

Example 1

Separation and Isolation of Toxins from *Bacillus Thuringiensis* var. Kurstaki NRD-12 Multigene Strain 1. Purification of parasporal crystals Purified crystals were prepared following literature procedures (e.g. Carey et al. Biochim Biophys. Acta, 872, 169 (1986))

2. Tryptic digestion 20 mg/mL NRD-12 crystal suspension in 0.1M CAPS/NaOH, pH 10.5 buffer was treated with 1 mg/mL commercial pancreatic trypsin. The reaction mixture was stirred at room temperature overnight and centrifuged at 10,000 rpm for 15 min. The decanted supernatant was filtered through a 0.22 μm cut-off membrane.

3. HPLC separation using a weak anion-exchanger

The separation was carried out using Waters 990 solvent delivery system equipped with an automatic injector and a photodiode array detector. Protein PAK DEAE 5PW anion exchange column (7.5×75 mm analytical or 21.5×150 mm semipreparative, Waters) was used; injection volume—1-20,000 μL; flow rate—4 mL/min.

Complex elution gradients employed 3 buffers:
A: 0.05M CAPS pH 10.5
B: 0.05M CAPS pH 10.5+0.17M NaCl
C: 0.05M CAPS pH 10.5+0.5M NaCl

| | Gradient table: | | | |
|---|---|---|---|---|
| Time [min.] | Flow [mL/min.] | % A | % B | % C |
| Initial | 4.00 | 100.0 | 0.0 | 0.0 |
| 20.00 | 4.00 | 0 0 | 100.0 | 0.0 |
| 35.00 | 4.00 | 0.0 | 100.0 | 0.0 |
| 50.00 | 4.00 | 0.0 | 90.0 | 10.0 |
| 55.00 | 4.00 | 0.0 | 90.0 | 10.0 |
| 60.00 | 4.00 | 0.0 | 0.0 | 100.0 |
| 65.00 | 4.00 | 0.0 | 0.0 | 100.0 |
| 70.00 | 4.00 | 100.0 | 0.0 | 0.0 |
| 79.90 | 4.00 | 100.0 | 0.0 | 0.0 |
| 80.00 | 0.50 | 100.0 | 0.0 | 0.0 |

Figure 2:
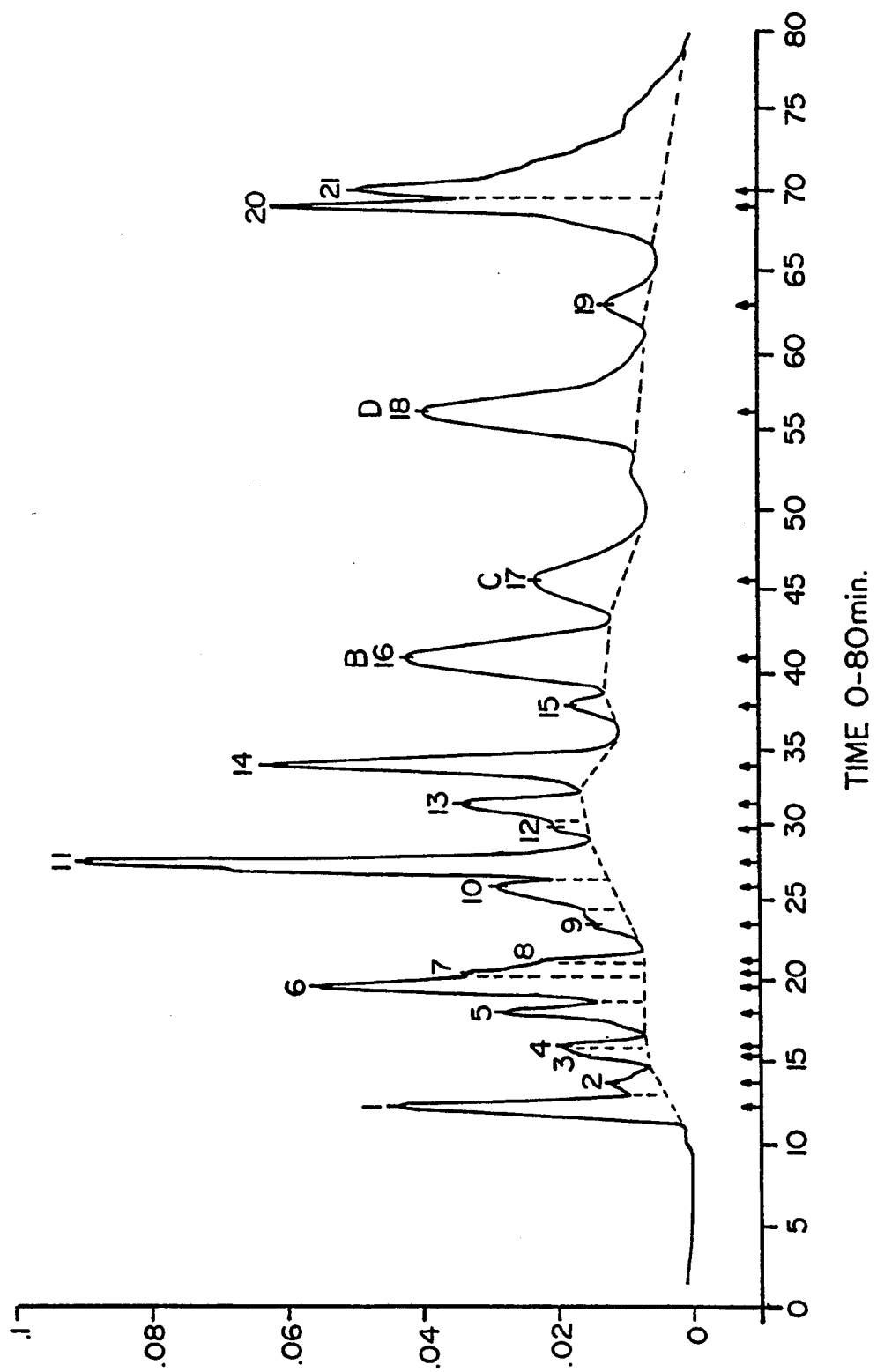
FIG. 2 represents a chromatogram obtained with Protein PAK DEAE 5 PW semipreparative column, under gradient conditions of FIG. 1 of a tryptic digest of parasporal crystals of the Bt kurstaki NRD-12 strain.

The employed gradient conditions are shown in FIG. 1. FIG. 2 shows a chromatogram of the tryptic digest under these gradient conditions, where the peaks of separated toxins are marked as B, C and D. Peak B corresponds to the cryIA(a)[4.5] gene toxin, peak C corresponds to the cryIA(b)[5.3] gene product and peak D represents the cryIA(c)[6.6] gene product. The condition of the column or very slight changes of pH or salt concentration can result in the shifting of the retention time of certain proteins by several minutes. As can be seen from FIG. 2 the separation takes place during approximately the first 60 minutes of elution. The following elution is for cleaning and regeneration of the column for subsequent separations.

Figure 8:
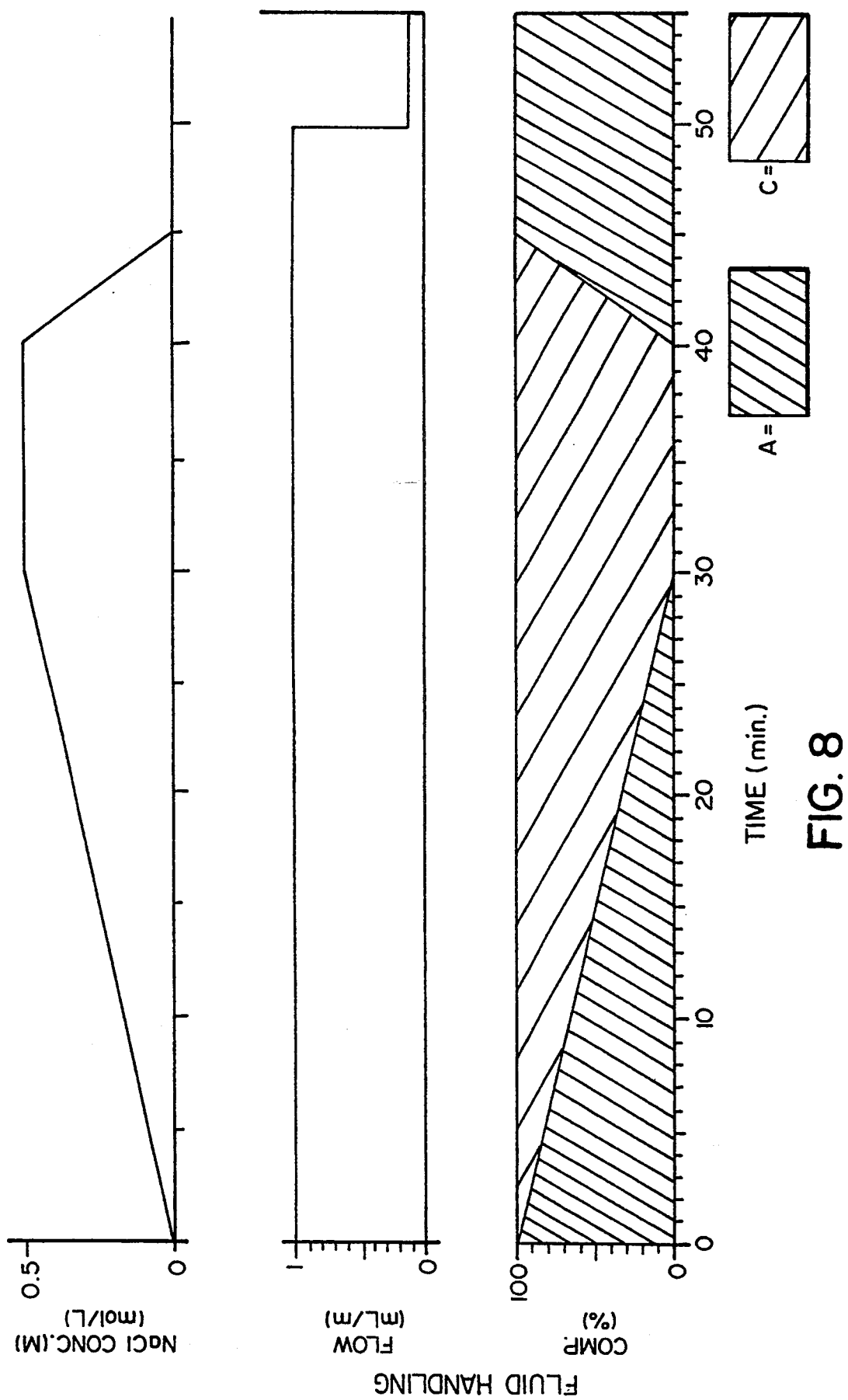
FIG. 8 represents gradient conditions of chromatographic separation shown in FIG. 9.
Figure 9:
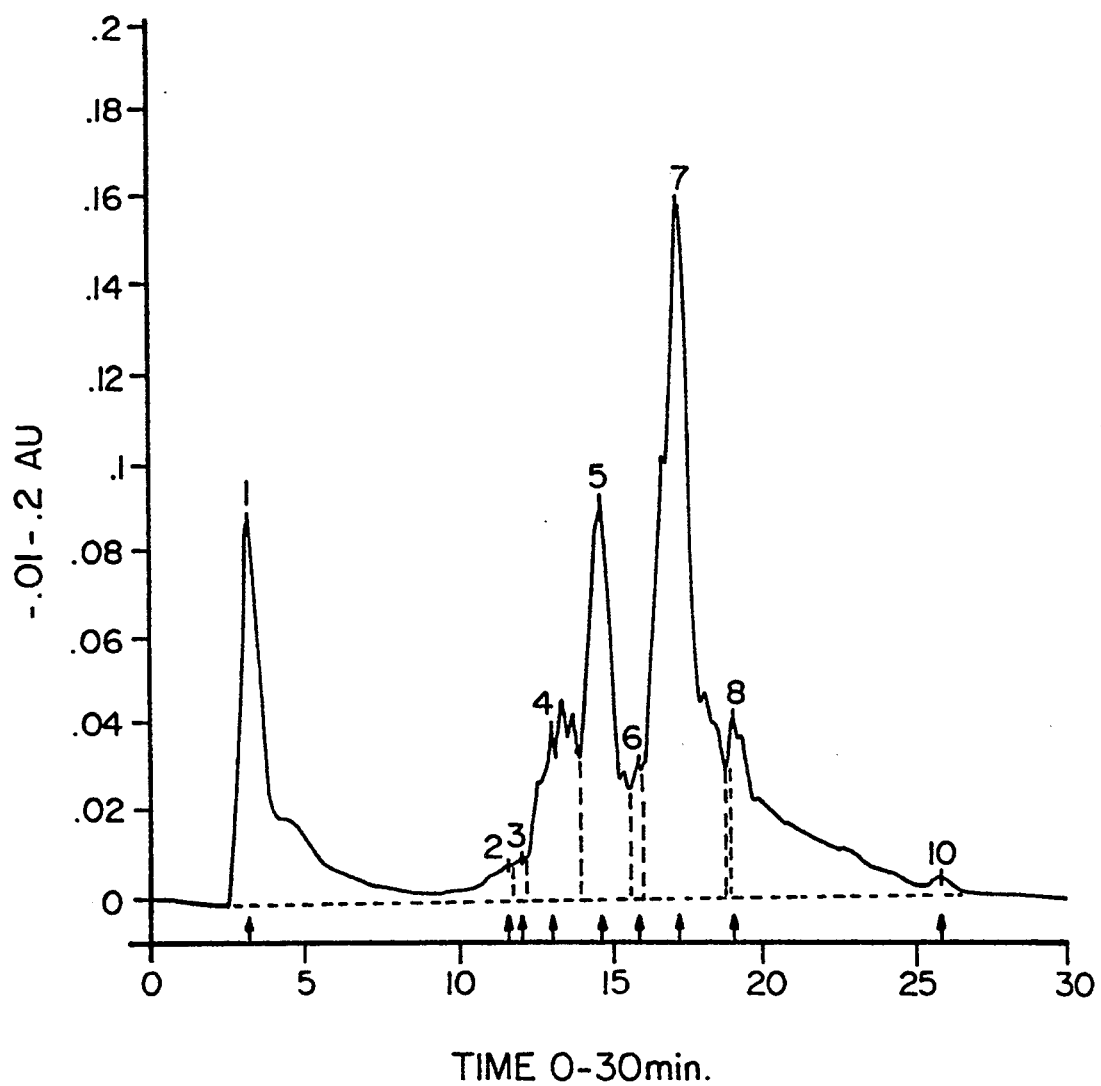
FIG. 9 represents a chromatogram similar to that represented by FIG. 2 and obtained with a Protein PAK DEAE column under gradient conditions of FIG. 8 (toxin peaks not resolved)

In a comparative test, no separation of the toxins was observed when a linear gradient of salt concentration increasing from 0 to 0.5M during 30 minutes was employed for the Protein PAK DEAE 5PW analytical column, as illustrated by FIG. 8. The chromatogram of the tryptic digest under these gradient conditions is shown in FIG. 9. The area around peak 7 contains the toxins.

4. Toxin isolation and purification

Figure 3:
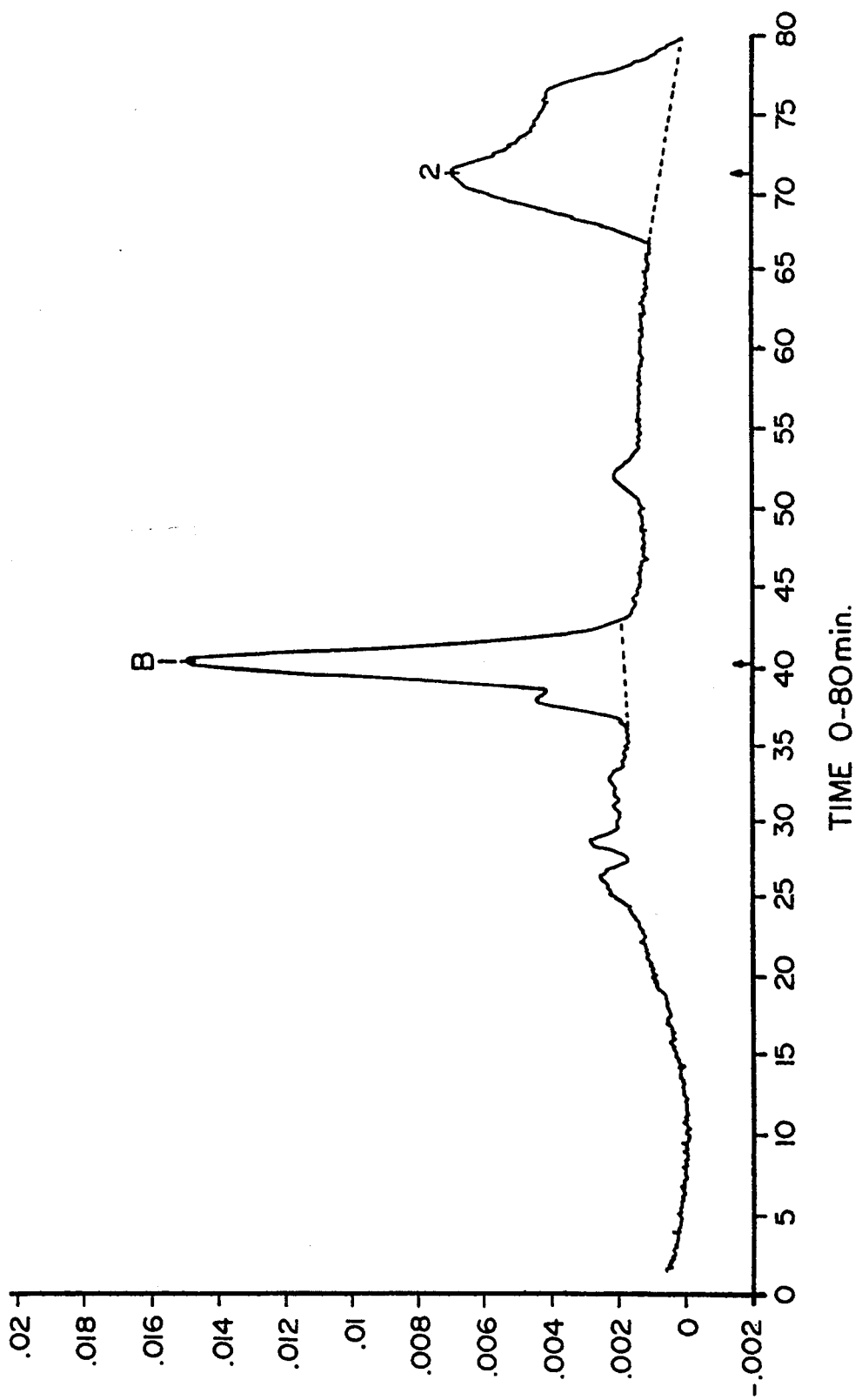
FIGS. 3, 4 and 5 represent chromatograms obtained under gradient conditions of FIG. 1 of components B, C and D of FIG. 2, respectively, reinjected after isolation.
Figure 4:
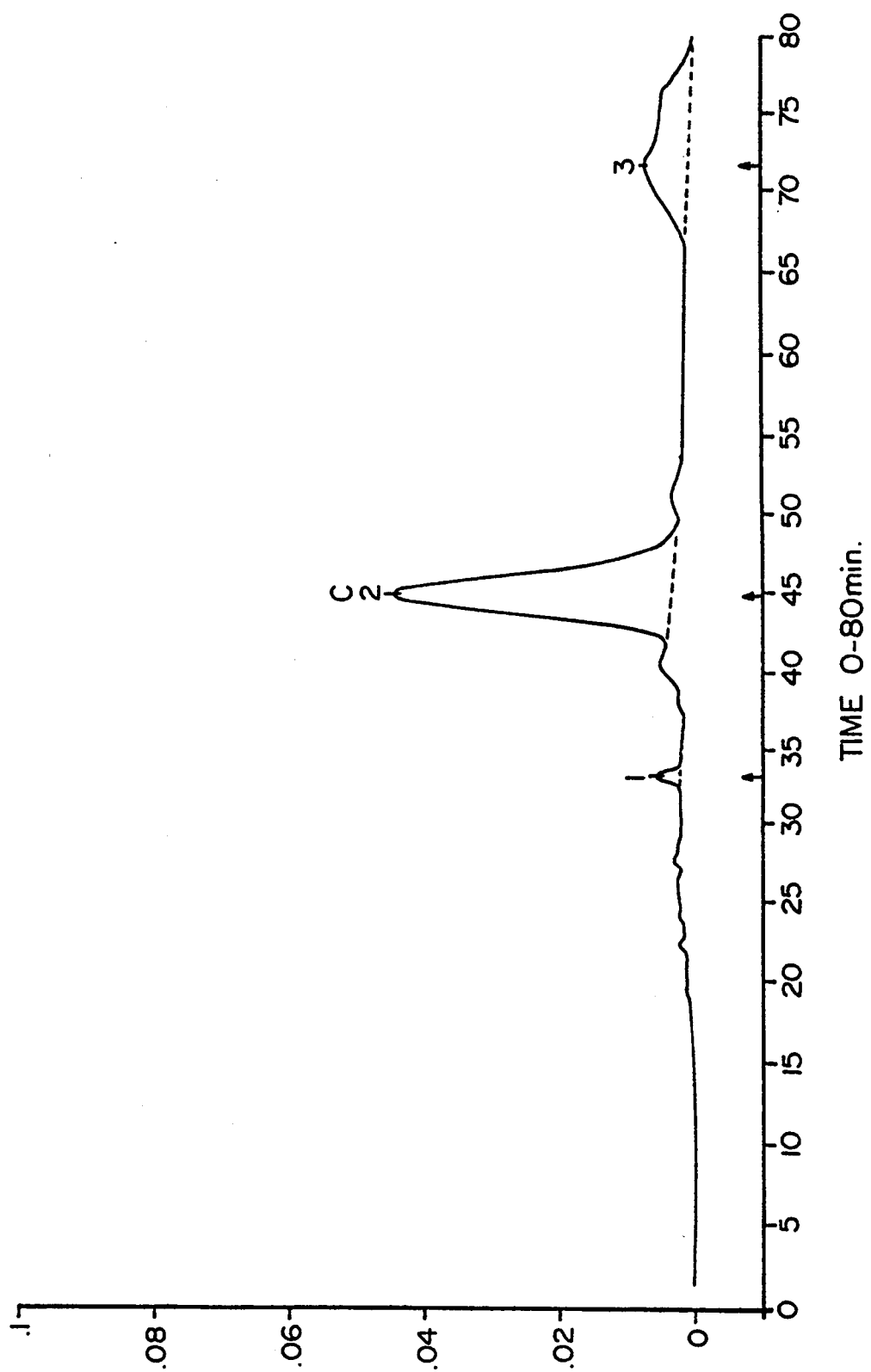
Figure 5:
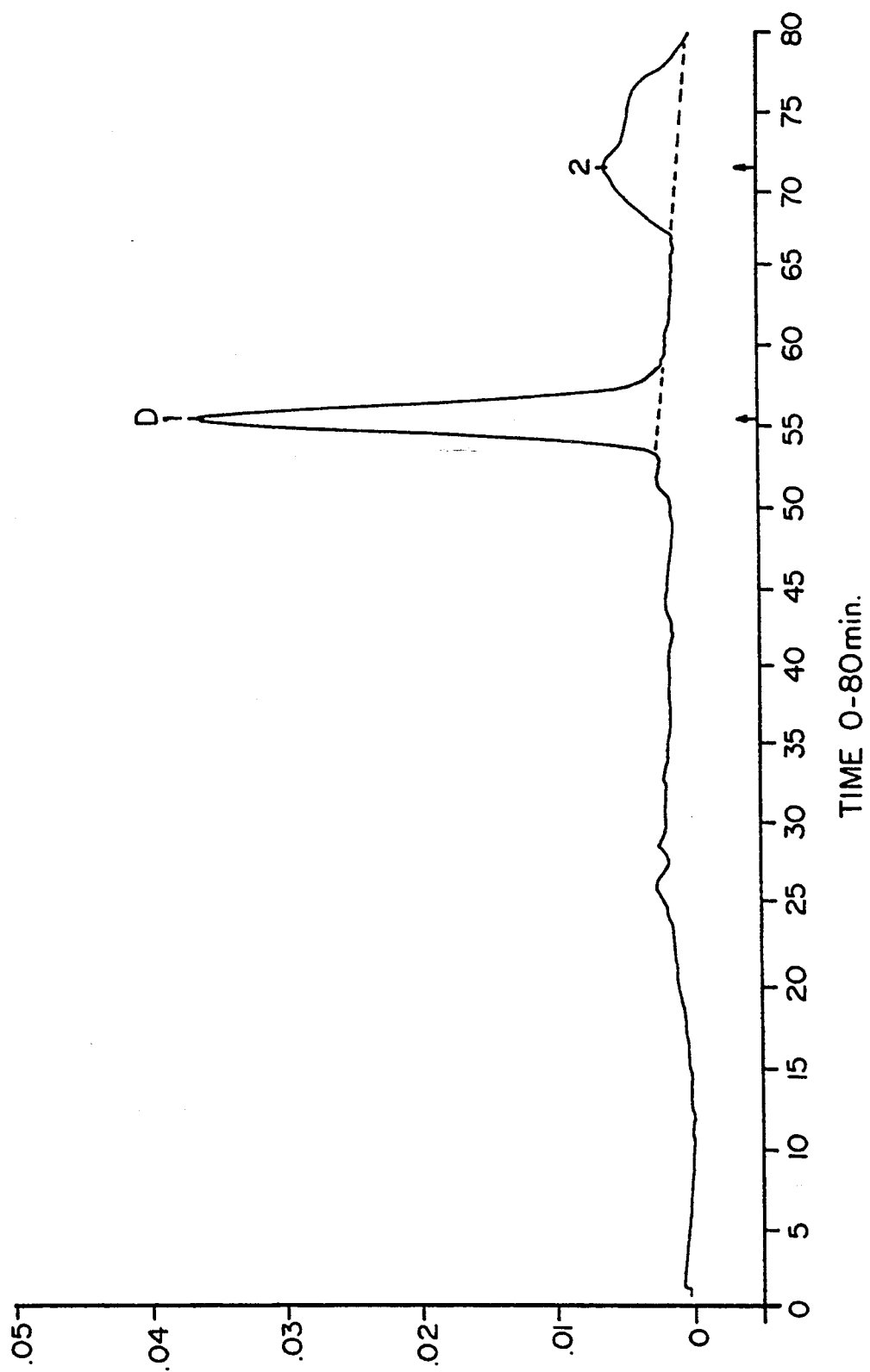

Parts corresponding to B, C and D candidate peaks were collected from the HPLC eluate, concentrated using 8 kDa polyethylene glycol/3.5 kDa cut-off dialysis tubing and reinjected into the HPLC column to establish purity. The respective chromatograms are shown in FIGS. 3, 4 and 5. With repeated injection-isolation procedure 100% purity of the isolated toxins can be achieved.

5. Confirmation of toxin identification

Toxins isolated and purified as described above were cleaved using CNBr and the resulting fragments were subjected to SDS-polyacrylamide gel electrophoresis (SDS-PAGE). The gel was electroblotted onto polyvinylidene difluoride membrane. The peptide bands in the membrane were stained, the visualized peptide bands were excised and candidate fragments were sequenced by an Applied Biosystems 475A protein sequencing system comprising a 470A gas phase sequencer equipped with an on-line 120A PTH analyser with a 900A control/data analysis module.

For the three gene strain of Bt var. *kurstaki* NRD-12 three candidate proteins were isolated from the HPLC eluate (peaks B, C, D in FIG. 2 and in FIGS. 3, 4 and 5, respectively). For these proteins SDS-PAGE showed three different patterns of cleavage. Sequencing of individual bands within each cleavage pattern demonstrated amino acid sequences which corresponded to unique sequences for each of the three toxins. These sequences are known from experimentally determined DNA sequences of the respective genes.

FIGS. 10A and 10B show the sequences of the three toxins activated by trypsin and aligned according to identical sequence segments, identified respectively as cryIA(a)[4.5], cryIA(b)[5.3] and cryIA(c)[6.6]. The sequences underlined in FIGS. 10A and 10B correspond to peptides which have been isolated and sequenced and most of which contain amino acid sequences unique to only one protein.

6. Bt strains examined

In the manner described above the toxin content of the following strains of Bt was examined:
Bt var. *kurstaki* HD-1 (3 proteins)
Bt var. *kurstaki* NRD-12 (3 proteins)
Bt var. *kurstaki* HD-73 (1 protein)
Bt var. *entomocidus* (2 proteins)
Bt var. *aizawai* HD-133 (2 proteins)
Bt var. *kurstaki* A20 (3 proteins)
and three *E. coli* clones, each containing a single Bt gene and giving rise to a single toxin product. Each of these genes corresponds to one of the three genes in the natural HD-1 strain. The HPLC retention times for the *E. coli* toxins and corresponding HD-1 toxins were identical.

7. Alternative HPLC separation using a strong anion exchanger

This separation was carried out using a MonoQ HR 5/5 (Pharmacia) anion exchange column having —CH$_2$—N(CH$_3$)$_3$ charged groups; injection volume 1-20,000 L; flow rate—1 mL/min.

The elution gradient employed 2 buffers:

A: 0.05M CAPS pH=10.5
B: 0.05M CAPS pH=10.5+0.5M NaCl

| Gradient table: | | | |
|---|---|---|---|
| Time [min.] | Flow [mL/min.] | % A | % B |
| Initial | 1.0 | 100.0 | 0.0 |
| 35.00 | 1.0 | 0.0 | 100.0 |
| 40.00 | 1.0 | 0.0 | 100.0 |
| 45.00 | 1.0 | 100.0 | 0.0 |
| 49.99 | 1.0 | 100.0 | 0.0 |
| 50.00 | 0.1 | 100.0 | 0.0 |

Figure 6:
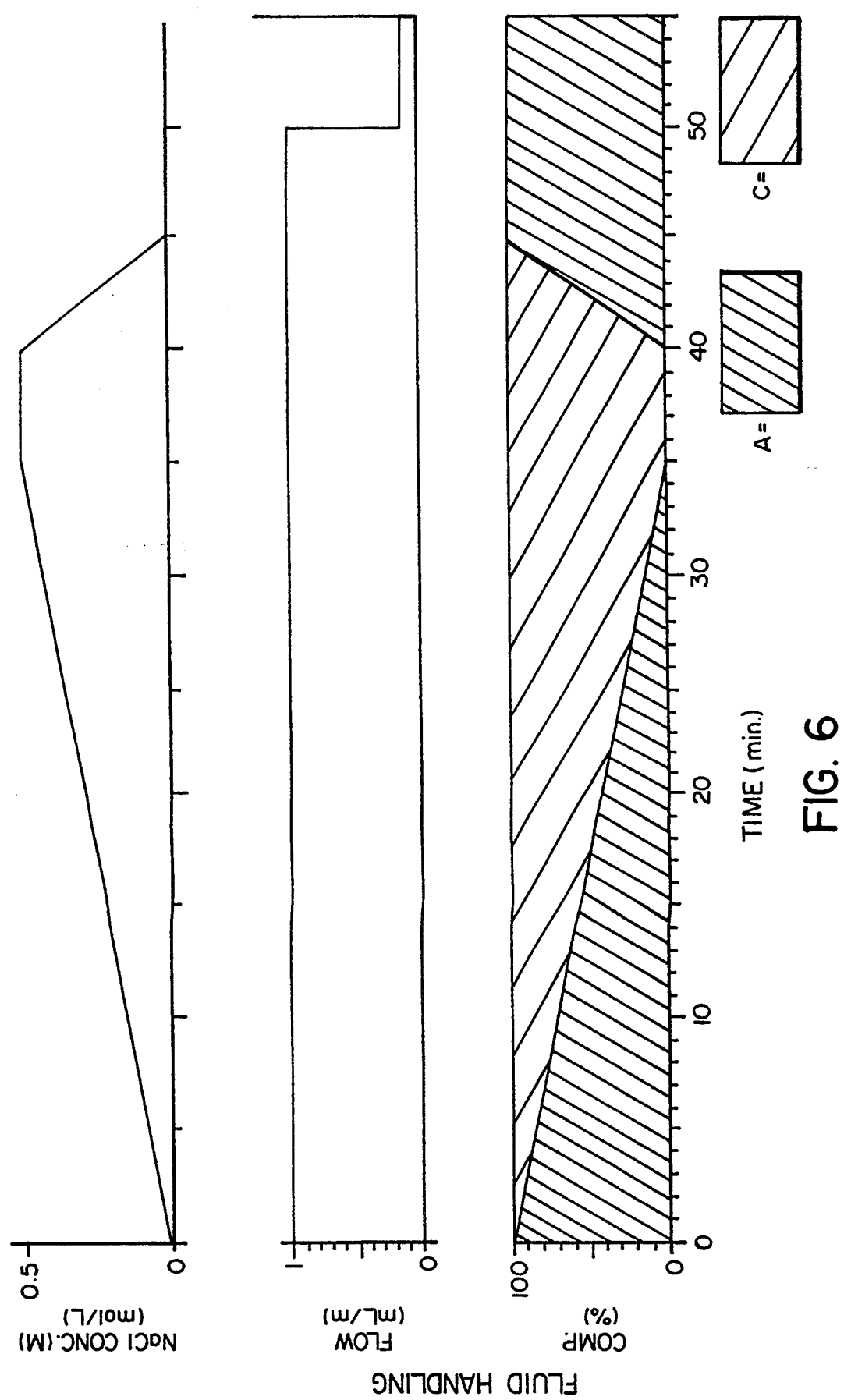
FIG. 6 represents gradient conditions of chromatographic separation according to another preferred embodiment of the invention, using a MonoQ column.
Figure 7:
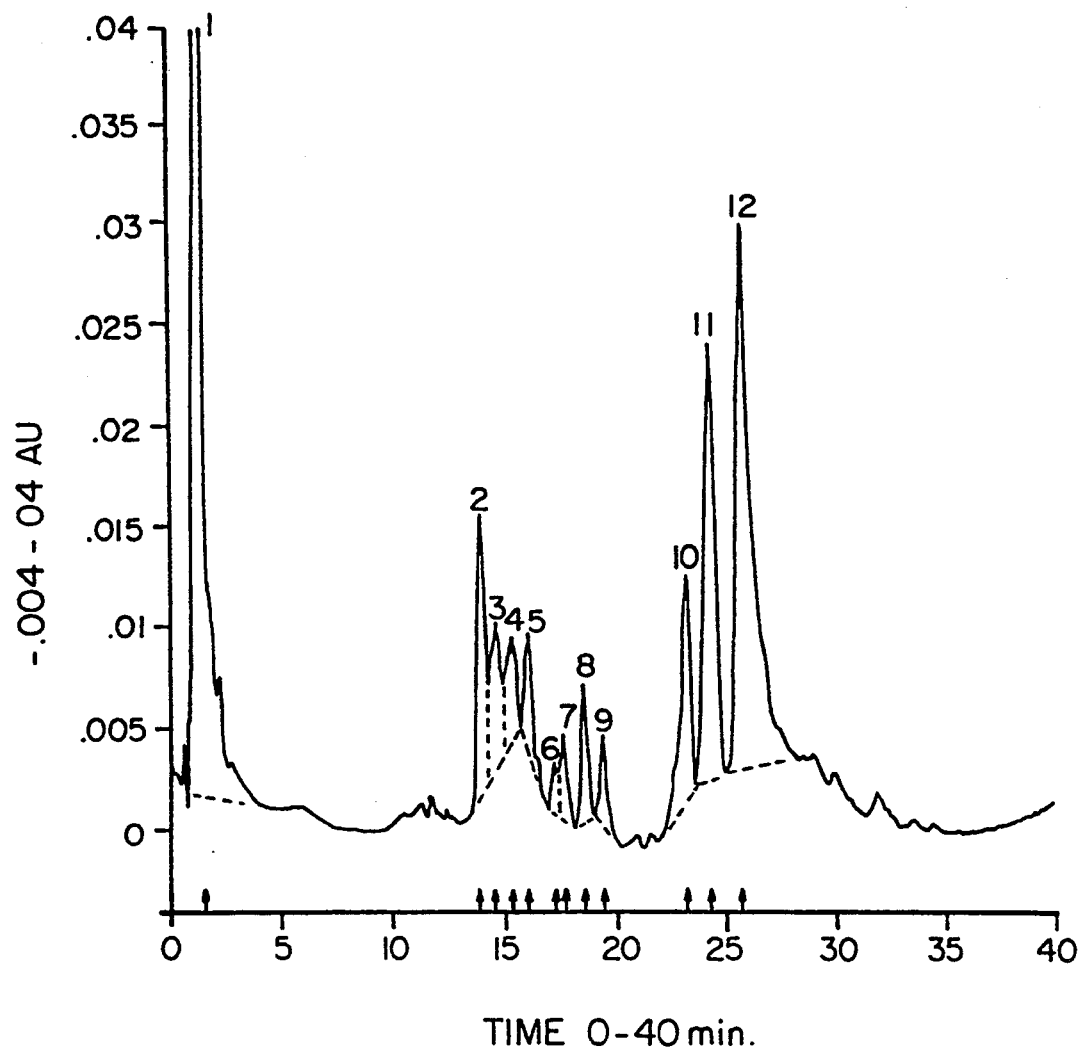
FIG. 7 represents a chromatogram obtained with a MonoQ column, under gradient conditions of FIG. 6 of a tryptic digest of parasporal crystals of a Bt kurstaki NRD-12 strain.

The employed gradient conditions are shown in FIG. 6. FIG. 7 shows a chromatogram of the tryptic digest under these gradient conditions, where peaks 10, 11 and 12, appearing approximately between 22 and 28 minute of the elution, correspond to separated toxins being cryIA(a)[4.5], cryIA(b)[5.3] and cryIA(c)[6.6] gene products. As can be seen from FIG. 6, the separation takes place under a linear gradient of sodium chloride increasing from 0 to 0.5M during 35 minutes.

Example 2

The following Bt strains were analysed and gene products identified, using the same methodology as in example 1, with the exception that the elution was effected using two buffers, according to the following gradient table. The weak anion exchanger was also employed
A: 0.05M CAPS/NaOH pH 11.5
B: 0.05M CAPS/NaOH+0.5M NaCl pH 11.5

| Gradient table for analytical scale: | | | |
|---|---|---|---|
| Time [min] | Flow [ml/min] | A % | B % |
| Initial | 1 | 100 | 0 |
| 2 | 1 | 100 | 0 |
| 40* | 1 | 67 | 33 |
| 41 | 0.5 | 67 | 33 |
| 60 | 0.5 | 67 | 33 |
| 61 | 1 | 67 | 33 |
| 65 | 1 | 0 | 100 |
| 70 | 1 | 100 | 0 |
| 71 | 0.1 | 100 | 0 |

*The gradient time can vary between 25–40 min depending on the nature of sample

The results were confirmed by microsequencing and bioassay:

| Strain | Expressed gene | Relative Ratio % |
|---|---|---|
| Bt var kurstaki HD -1 | cryIA(a) | 28 |
| | cryIA(b) | 39 |
| | cryIA(c) | 33 |
| Bt var kurstaki NRD-12 | cryIA(a) | 41 |
| | cryIA(b) | 36 |
| | cryIA(c) | 23 |
| Bt var kurstaki A-20 | cryIA(a) | 17 |
| | cryIA(b) | 17 |
| | cryIA(c) | 66 |
| Bt var entomocidus | cryIA(a) | 40 |
| | cryIA(b) | <5 |
| | cryIA(c) | <5 |
| | cryIB | <5 |
| | cryIC | 50 |
| Bt var kurstaki HD-73 | cryIA(c) | 100 |
| HD-2 | cryIC (+4 other proteins) | 25 |
| Bt var thuringiensis | cryIB | |
| Bt var tenebrionis | cryIIIA | >90 |
| Bt var israelensis | cytA (+4 other proteins) | 30 (in cryIVC+ D mixture) |

What we claim as our invention is:

1. A process for separating and identifying proteinaceous protoxins expressed by a multi-gene strain of *Bacillus thuringiensis*, which process comprises the steps of:
   providing a material comprising biologically active protoxins of *Bacillus thuringiensis*;
   subjecting said material comprising said biologically active protoxins of *Bacillus thuringiensis* directly to hydrolysis with a proteolytic enzyme in an aqueous suspension at a pH in the range of 10–12, to generate a mixture of solubilized daughter toxins in biologically active state, said hydrolysis being carried out for a time sufficient to assure substantially complete liberation of said toxins;
   subjecting said mixture of solubilized daughter toxins to high performance anion-exchange liquid chromatography at a substantially constant pH in the range of 10–12, and under aqueous conditions corresponding to the use of a first eluent containing only a buffer and the gradual introduction over a predetermined period of time of at least one other eluent containing the buffer and a suitable salt, the changes in time of the concentration of the salt in the at least one other eluent being such that the daughter toxins, in biologically active state, are separated from each other and from other products of hydrolysis; and
   identifying and where required quantifying the protoxins from the chromatographic signals produced by the daughter toxins.

2. The process according to claim 1, wherein the strain is a known strain and the process is used to determine the level of expression of the protoxins and the viability of the strain.

3. The process according to claim 1, wherein the proteinaceous protoxins are expressed by cloned *Bacillus thuringiensis* genes.

4. The process according to claim 1, which further comprises the step of isolating and purifying an individual toxin in biologically active state.

5. The process according to claim 1, wherein said material comprising biologically active protoxins is parasporol crystals of *Bacillus thuringiensis*.

6. The process according to claim 1, wherein said material comprising biologically active protoxins is a crude fermentation mixture of *Bacillus thuringiensis* separated from the fermentation broth.

7. The process according to claim 1, wherein said proteolytic enzyme is trypsin, and the duration of hydrolysis is about 10 minutes to 12 hours.

8. The process according to claim 1, wherein the proteolytic enzyme is selected from the group consisting of trypsin, chymotrypsin, elastase and insect gut juices.

9. The process according to claim 8, wherein the proteolytic enzyme is trypsin.

10. The process according to claim 9, wherein the hydrolysis is carried out directly at a pH of about 10.5.

11. The process according to claim 10, wherein the chromatography is carried out in 0.05M 3-cyclohexylamino-1-propanesulfonic acid/NaOH buffer.

12. The process according to claim 10, wherein the hydrolysis is carried out in 0.1M 3-cyclohexylamino-1-propanesulfonic acid/NaOH buffer.

13. The process according to claim 12, wherein the chromatography is carried out at a pH of 10.5 to 11.5.

14. The process according to claim 10, wherein the hydrolysis is carried out at a temperature of from about 20° to about 40° C.

15. The process according to claim 4, wherein the salt is sodium chloride.

16. The process according to claim 1, wherein the anion exchanger is a weak anion exchanger.

17. The process according to claim 16, wherein the anion exchanger is diethylaminoethyl poly(methyl methacrylate).

18. The process according to claim 1, wherein the anion exchanger is a strong anion exchanger.

19. The process according to claim 18, wherein the anion exchanger contains trimethylammoniummethyl groups.

20. The process according to claim 1, wherein the chromatography is carried out at a pH substantially the same as the pH at which the hydrolysis is conducted.

21. The process according to claim 20, wherein the solution after hydrolysis is subjected directly to chromatography.

22. The process according to claim 1, wherein the high performance liquid chromatographic signals are identified by comparing with chromatographic signals obtained by subjecting a protoxin expressed by a known *Bacillus thuringiensis* gene to hydrolysis with the same proteolytic enzyme under the same conditions, followed by anion exchange high performance liquid chromatography under the same conditions.

23. The process according to claim 1, wherein said material comprising biologically active protoxins is hydrolyzed with trypsin in 0.1M 3-cyclohexylamino-1-propanesulfonic acid/NaOH buffer having a pH of 10.5, the solution after hydrolysis is subjected directly to chromatography on diethylamino poly(methyl methacrylate), the first eluent is 0.05M 3-cyclohexylamino-1-propanesulfonic acid/NaOH buffer having a pH of 10.5, a second eluent containing the same buffer as said first eluent and containing 0.17M sodium chloride is introduced simultaneously with said first eluent in such manner that the amount of the second eluent increases linearly from 0 to 100% over a period of approximately 20 minutes, and a third eluent containing the same buffer as said first eluent and 0.5M sodium chloride is introduced commencing approximately 50 minutes after the amount of said second eluent has reached 100% wherein the amount of the third eluent increases linearly from 0 to 100% over a period of approximately 15 minutes.

24. The process according to claim 1, wherein said material comprising biologically active protoxins is hydrolyzed with trypsin in 0.1M 3-cyclohexylamino-1-propanesulfonic acid/NaOH buffer having a pH of 10.5, the solution after hydrolysis is subjected directly to chromatography on a resin containing trimethylammoniummethyl groups, the first eluent is 0.05M 3-cyclohexylamino-1-propanesulfonic acid/NaOH buffer having a pH of 10.5, and a second eluent containing the same buffer as said first eluent and 0.5M sodium chloride is introduced simultaneously with said first eluent in such a manner that the amount of the second eluent increases linearly from 0 to 100% over a period of approximately 35 minutes.

25. The process according to 1, wherein said material comprising biologically active protoxins is hydrolyzed with trypsin in 0.1M 3-cyclohexylamino-1-propanesulfonic acid/NaOH buffer having a pH 10.5, the solution after hydrolysis is subjected directly to chromatography on a resin containing trimethylammoniummethyl groups, the first eluent is 0.05M 3-cyclohexylamino-1-propanesulfonic acid/NaOH buffer having a pH of 11.5, and a second eluent containing the same buffer as said first eluent and 0.5M sodium chloride is introduced simultaneously with said first eluent in such a manner that the amount of the second eluent increases linearly from 0 to 100% over a period of approximately 40 minutes.

* * * * *